United States Patent
Robst et al.

(10) Patent No.: US 10,045,879 B2
(45) Date of Patent: Aug. 14, 2018

(54) PORTABLE HYPO/HYPERTHERMIA UNIT

(71) Applicant: Geratherm Medical AG, Geschwenda (DE)

(72) Inventors: Thomas Robst, Geschwenda (DE); Gert Frank, Geschwenda (DE); Ronald G. LeTourneau, Canton, MI (US)

(73) Assignee: Geratherm Medical AG, Geschwenda (DE)

( * ) Notice: Subject to any disclaimer, the term of this patent is extended or adjusted under 35 U.S.C. 154(b) by 1075 days.

(21) Appl. No.: 14/102,924

(22) Filed: Dec. 11, 2013

(65) Prior Publication Data
US 2015/0157495 A1 Jun. 11, 2015

(51) Int. Cl.
| A61F 7/00 | (2006.01) |
| A61F 7/10 | (2006.01) |
| A61F 7/02 | (2006.01) |

(52) U.S. Cl.
CPC ............ *A61F 7/0085* (2013.01); *A61F 7/007* (2013.01); *A61F 7/10* (2013.01); *A61F 7/02* (2013.01); *A61F 2007/0009* (2013.01); *A61F 2007/0054* (2013.01); *A61F 2007/0076* (2013.01); *A61F 2007/0078* (2013.01)

(58) Field of Classification Search
CPC .................... A61F 7/007; A61F 7/0085; A61F 2007/0075; A61F 2007/0054; A61F 2007/009; A61F 2007/0078; A61F 2007/008; A61B 2018/1226
See application file for complete search history.

(56) References Cited

U.S. PATENT DOCUMENTS

| 5,072,875 A | 12/1991 | Zacoi |
| 5,507,792 A | 4/1996 | Mason et al. |
| 5,913,885 A | 6/1999 | Klatz et al. |
| 6,612,309 B1 * | 9/2003 | Ancona ............ A61M 16/0465 128/207.14 |
| 7,022,093 B2 | 4/2006 | Smith et al. |
| 7,637,931 B2 | 12/2009 | Heaton |
| 7,914,563 B2 | 3/2011 | Mason et al. |

(Continued)

FOREIGN PATENT DOCUMENTS

| EP | 0 620 655 A2 | 10/1994 |
| JP | 2006230761 A | 9/2006 |

(Continued)

OTHER PUBLICATIONS

European Search Report for Application No. EP14197203, Completed by the European Patent Office dated Jun. 3, 2015 together 10 Pages.

*Primary Examiner* — Linda Dvorak
*Assistant Examiner* — Yasamin Ekrami
(74) *Attorney, Agent, or Firm* — Brooks Kushman P.C.

(57) ABSTRACT

A portable heating/cooling device for clinical hypo/hyperthermia with cuffs especially designed for arterial cooling/heating for raising or lowering the body temperature of a patient is operable by battery power or a wide range of available external power, and is usable in the field or in medical transport where such external power sources are not available. The small size, weight, and robust nature of the device allows it to be transported with the patient without the need for additional conveying devices.

6 Claims, 3 Drawing Sheets

(56) References Cited

U.S. PATENT DOCUMENTS

| | | | |
|---|---|---|---|
| 7,959,657 B1* | 6/2011 | Harsy | A61F 7/007 607/104 |
| 2002/0026226 A1* | 2/2002 | Ein | A61F 7/007 607/108 |
| 2002/0103520 A1 | 8/2002 | Latham | |
| 2003/0160063 A1* | 8/2003 | Paukovits | A61J 7/0053 222/129 |
| 2004/0158303 A1* | 8/2004 | Lennox | A61F 7/0085 607/109 |
| 2008/0228248 A1 | 9/2008 | Guyuron et al. | |
| 2010/0163023 A1* | 7/2010 | Singh | A61M 16/04 128/200.26 |
| 2012/0179230 A1 | 7/2012 | Ramirez Barrones et al. | |

FOREIGN PATENT DOCUMENTS

| | | |
|---|---|---|
| WO | 94/00086 A1 | 1/1994 |
| WO | 98/56310 A1 | 12/1998 |

* cited by examiner

PORTABLE HYPO/HYPERTHERMIA UNIT

BACKGROUND OF THE INVENTION

1. Field of the Invention

The invention pertains to a portable hypo/hyperthermia unit suitable for clinical medical use in cooling or heating selected portions of the body of a patient, to raise or lower the temperature thereof, particularly for cooling or heating at arterial sites.

2. Description of the Related Art

There are numerous circumstances in the medical field where raising or lowering the temperature of the body of a patient is warranted. As indicated in U.S. Pat. No. 7,637,931, for example, mild hypothermia (32-34° C., for instance) has proven to be successful in reducing neural damage from stroke, heart attack, head trauma, etc. Reduction of brain temperature by the use of helmets provided with means for circulating cool air or fluids have been disclosed, for example in U.S. Pat. No. 5,913,885 and PCT Published Application WO 98/56310. In U.S. Pat. No. 7,637,931, such devices, and also cooling pillows, have been described as unsatisfactory, particularly because of their bulk and specialized knowledge required for their use. U.S. Pat. No. 7,637,931 proposes to solve these problems by providing a shroud which, for example, encloses the head or even the entire body of the patient. Air is cooled or heated by Peltier effect devices and a series of valves which flow air over the cooling side of the Peltier device, over the heating side, or which bypasses the device altogether. The air is circulated by a blower through the shroud, where it cools or heats the body or respective body part. Such devices, however, are also bulky, and must rely on relatively large air passages to provide a volume of air necessary for the desired cooling effect. At times, it is considered medically advisable to raise body temperature, or to alternate heating and cooling.

Smith et al., in U.S. Pat. No. 7,022,093, discuss the disadvantages of using cooling devices such as gel packs, ice bags, etc., and proposes instead to use a brace or "wrap" which incorporates Peltier effect cooling devices which directly cool the body located within the brace. Disadvantages of such devices are that they are implemented for specific body parts, each requiring a different brace, and that the devices are relatively expensive. If the device is to be reused, it must be sterilized, or the Peltier elements and associated electronics must be removed and inserted into a new brace, which may also involve sterilization of the Peltier elements themselves.

Barrones et al. U.S. Published Application 2012/0179230 discloses a device for performing beauty treatments, physiotherapy, and hydrotherapy which employs Peltier devices for cooling of a fluid which is then circulated to a heat exchange device such as a face mask. When heating of the fluid is desired, or when the temperature of the cooled fluid is to be moderated, the fluid is passed through resistive heating units. The unit is complex, bulky, and due to the many internal parts, relatively expensive to manufacture. It is designed as a dedicated unit for stationary use, where it can be connected to a computer or LED screen for performance monitoring. The device cannot accompany a patient during transport, and is not designed for clinical use.

There has been a long felt need for a portable, self-contained device which is capable of performing both clinical hypothermia and hyperthermia, i.e. both cooling and heating of the body.

SUMMARY

The invention pertains to a portable, self-contained unit suitable for both clinical hypothermia and hyperthermia. The device contains a Peltier module which both heats and cools a circulating fluid on the same side of the Peltier module, a power module, a fluid reservoir, a fluid circulating pump, a battery power source, a control module, a display screen, fluid inlet and outlet ports, and a thermal cuff/pad for transferring heat to or from the body.

DETAILED DESCRIPTION

The inventive hypo/hyperthermia device is self-contained and portable. By "self-contained" is meant that with the exception of fluid transfer lines and thermal cuff/pads, the device is capable of operation without connection to external devices such as power supplies, liquid supply lines, computer monitors, etc. Thus, the device is suitable for use, inter alia, on the battlefield, in EMS units, med-evac helicopters, and other emergency vehicles, without modification or other external support. By portable is meant that the device is of such small size and weight that it may be easily transported without the need of a separate support device such as a wheeled cart, etc. The device may be located proximate to a patient's body or placed on a litter or gurney with the patient, for example.

Figure 1:
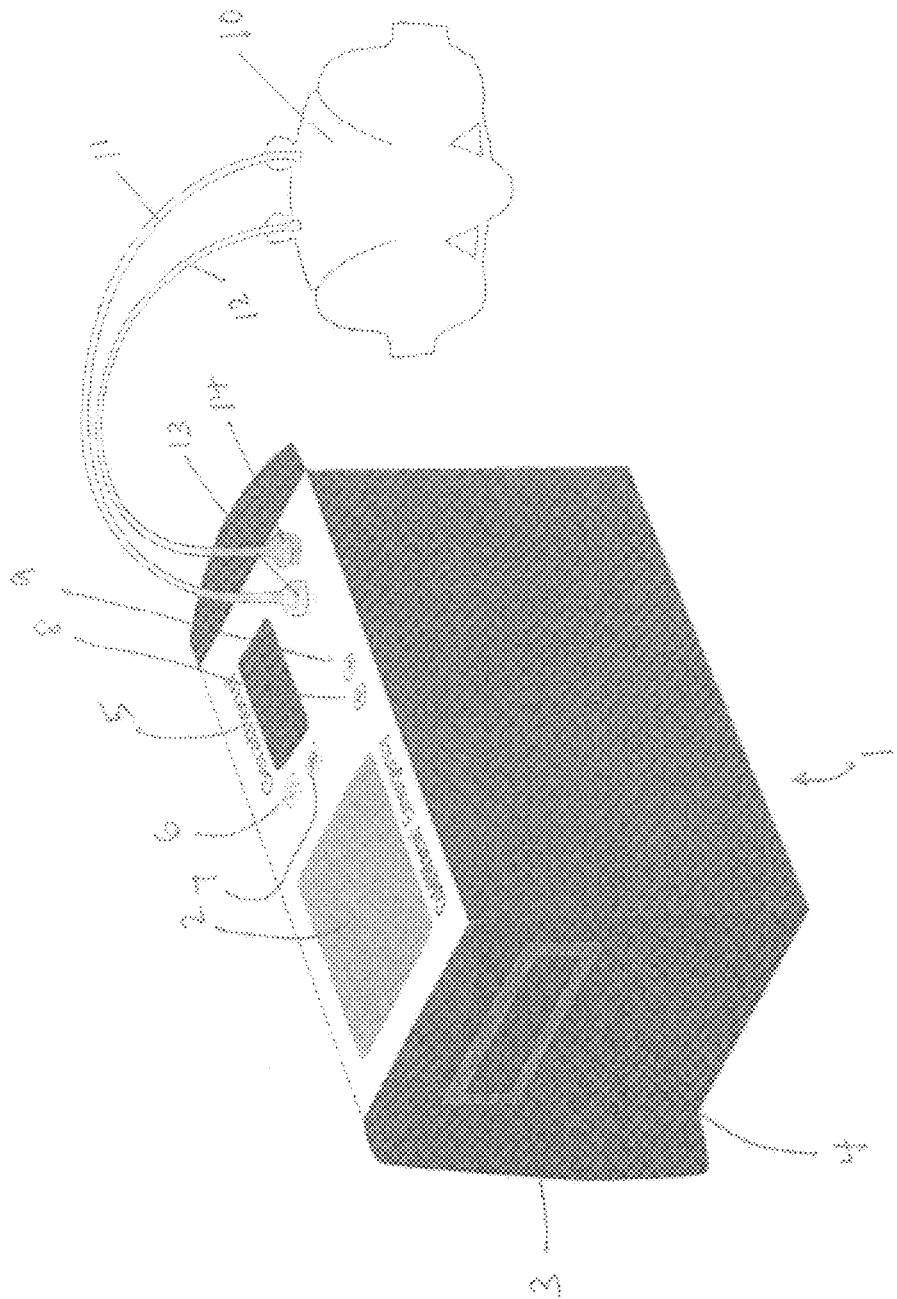
FIG. 1 illustrates one embodiment of a portable hypo/hyperthermia device of the invention.

FIG. 1 illustrates the small and portable nature of the inventive device. In this embodiment, opening 2 is of mesh construction and allows air to be drawn in from the outside by the internal fan, the air exiting at openings in the end sides of the device, one such opening 3 being shown in the drawing. At 4 is a hook and loop fastened flap which allows access to the replaceable batteries located below the flap. Alongside of the LED flat panel display 5 are heat/cool touch sensitive switches 6 and 7, and also on the front panel are on/off switches 8 and 9. An arterial cuff 10 having heating/cooling passages therein is attached to the heating/cooling module 1 by flexible tubes 11 and 12, terminating on their proximal ends by twist lock fluid connectors 13 and 14.

Figure 2:
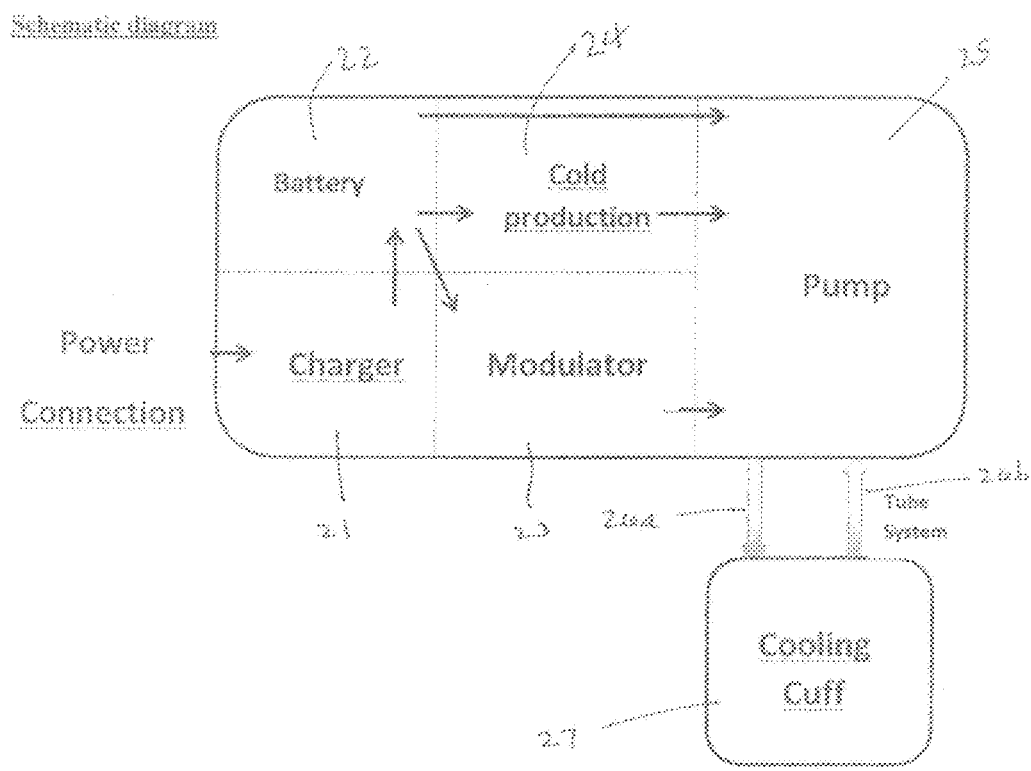
FIG. 2 illustrates one embodiment, in schematic form, of an inventive device.

FIG. 2 illustrates, in schematic form, operational elements within the heating/cooling module. The power control module, charger 21, is capable of changing battery 22 as well as accepting external electrical energy at various voltages, both AC and DC. The control module, or modulator 23 controls the Peltier module, pump, fan, and display, as described elsewhere herein. The Peltier module will likely be most often used in a cooing mode, and is labeled "cold production" 24 in the drawing. The pump 25 pumps heat transfer fluid from the Peltier module through tube system 26a, 26b, to arterial cooling cuff 27.

Figure 3:
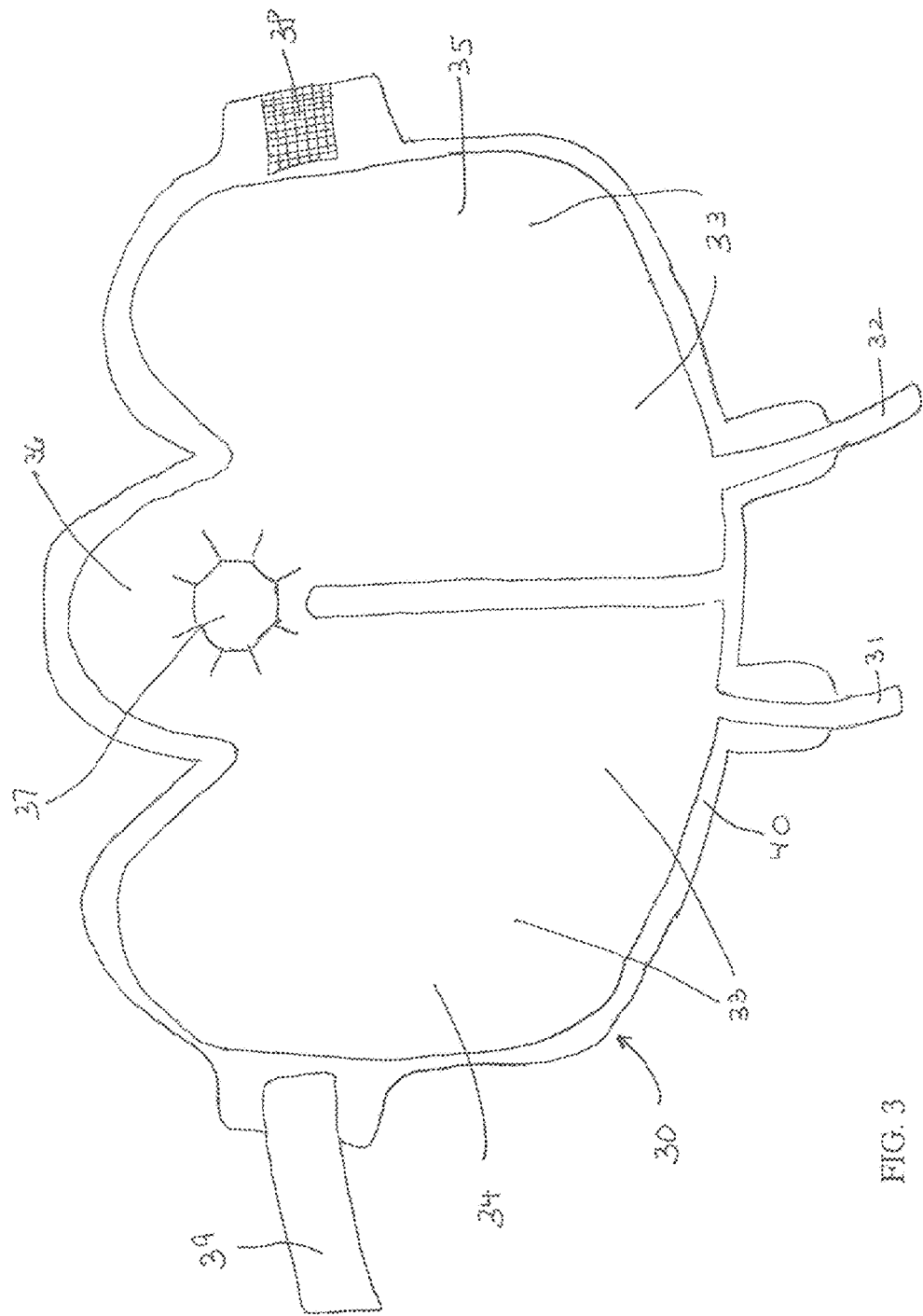
FIG. 3 illustrates one embodiment of a neck cuff of the invention.

FIG. 3 illustrates an arterial cooling cuff 30 suitable for use in the neck region of a patient, i.e. over the carotid artery. The cuff 30 has inlet 31 and outlet 32, which supply fluid to cooling passages 33. Flap portions 34 and 35 are adapted to surround the neck, while frontside portion 36 has a hole 37 which is positioned over the trachea, to receive a tracheotomy tube. Hook and loop fasteners 38 and 39 allow for securing the device around the neck of a patient. The top and bottom of the cuff are connected at the periphery 40 to prevent fluid escape, by molding, adhesive bonding, or thermal bonding, for example.

The inventive device includes a Peltier effect heating/cooling thermal module. Peltier effect devices are based on the discovery that when passing current through a junction of two different materials, heat is generated in one material side and removed from the other material. Peltier devices may be viewed as electronic heat pumps. Individual Peltier cells may be small, and in general, a number of such cells are packaged together, with their "cold" sides connected to a heat sink, and their "hot" sides connected to a further heat sink. It is noted that "heat sink" in the context of the invention is a thermal transfer element which may be hot or cold, not merely hot. One or a plurality of individual devices, or "sub-modules," each of which may contain a plurality of individual Peltier cells, constitute the thermal module. Such devices are commercially available from numerous sources, and have been used, e.g. to cool high power integrated circuits in computer applications, and imaging sensors in astronomical imaging systems, where the temperature of the sensor may be lowered to as much as 70° C. below ambient to reduce noise in the sensor.

In the present invention, the Peltier module is provided on one side with a heat sink containing passages for circulating a heat transfer fluid. The opposing side is connected to a normal heat sink designed to remove heat or to add heat by means of flow of air, directed over the heat sink by a small fan. The cooling or heating power delivered to the heat transfer fluid may be controlled by varying the electrical current to the Peltier elements. Thus, for example, when in the cooling mode, full power results in a high cooling capacity while low power results in a low cooling capacity. Upon initial use with a given patient, for instance, a high cooling capacity may be selected to rapidly cool the body, and once the desired body temperature is approached or achieved, the power may be decreased to maintain the desired temperature. Since heat transfer from the "cuff" or similar device will be in part determined by the temperature difference, $\Delta T$, between the body and the cuff, the temperature of fluid returning to the device as compared to that exiting the device is an indication of the degree of power which must be supplied, and this is controlled by the control module. The actual body temperature or regional body temperature may also be used in controlling the degree of cooling.

A unique feature of the present device is that the device may be set to a heating mode by simply reversing the direction of current flow through the device. When this is done, the heat sink containing heat transfer liquid passages is heated by the Peltier devices, producing a warm heat transfer liquid. As a result of this unique construction, a matrix of valves which change heat transfer liquid flow from one side of the Peltier module to the other side is not necessary. The reduction of multiple valves, check valves, and their associated fluid lines and circuitry results in an extremely simple, lightweight, compact, and robust device not previously possible. In a preferred embodiment, the device contains no valves at all. Resistive heating, which produces large current drain, is also not necessary.

The inventive device preferably uses a single Peltier module, but the use of a plurality of submodules is also possible, but not preferred. In inventive devices having a plurality of Peltier effect submodules, each submodule may optionally be controlled independently. In one such operating mode, for example, the current direction in at least one submodule may be such that cooling of the heat transfer fluid occurs, and a further submodule may be in a heating or cooling mode, for fine adjustment of the outlet fluid temperature. However, it is desirable that all submodules be operated in the same mode, with fine control of fluid temperature being accomplished by varying the current to all submodules together, at a given current direction. Furthermore, the fluid temperature and therefore the control of a single or a plurality Peltier element can be done by PPM.

The inventive device contains a pump to circulate heat transfer liquid. Any suitable type of pump may be used, including, but not limited to, membrane pumps, impeller pumps, vane pumps, centrifugal pumps, peristaltic pumps, bellows pumps, etc. The pump is electrically driven, and the electrical driving system is preferably unitary with the pump. The electrical driving system may, for example, include a direct or alternating current motor, a solenoid system, etc. The pump is preferably adjustable in output. The control module, for example, may raise or lower the pump speed, or turn off the pump entirely. The pump may be designed for any suitable pumping speed consistent with the portability of the inventive device. Useful flow rates in a circulatory mode, for example, may range from 0.01 l/min to 5 l/min, more preferably 0.1 to 2 l/min.

The inventive device preferably contains a fluid reservoir for heat transfer fluid, which may optionally be insulated. Alternatively, the circulation system, which includes the pump and associated fluid circulation lines will contain fluid. Fluid may be precontained in the circulation system or may be added at start up, e.g. through the device inlet port or a separate charging port. When the device contains no fluid reservoir, it is desirable that the heating/cooling cuffs be precharged with fluid, which can be drawn into the device upon connection of the cuff to the device.

The inventive device contains a replaceable battery, or is adapted with electrical connections and appropriate mechanical fastening means to receive a battery. The battery is rechargeable, and is most preferably of the nickel cadmium or lithium ion type. The battery or battery module, as appropriate, is replaceable. The ability to replace a spent battery in the field with a fresh battery extends the operational life and allows for thermal conditioning of a patient for extended periods even when no external power source is available. Any type of mechanical fastening means may be utilized, and numerous examples of such are present in numerous rechargeable devices, including flashlights, power tools, and the like. The replaceable battery is preferably secured by simple hinge-like or deformable latches so that replacement of the battery does not require any tools.

The inventive device preferably contains two replaceable batteries, and these are preferably used sequentially, the control module or power module detecting when the battery in use approaches its fully discharged state and automatically switching to the second battery. Thus, uninterrupted operation for extended periods of time is possible. In addition, the spent battery may be replaced with a fresh battery while the device is still performing its clinical function. The batteries are preferably lithium ion batteries nominally rated at 14.4 V and 5 ampere hours, more preferably greater than 6 ampere hours.

The inventive device contains a power supply module. The power supply module converts battery voltage, if appropriate, to one or more voltages necessary to operate the circulation pump, the Peltier module, the control module, the visual display, and any other electronic components, which may require different voltages. The power control module further contains battery recharging circuitry, and an inverter to convert standard 50-60 hz alternating current ("AC") in the range of, for example, 90-250 V, to direct current ("DC"), and also preferably capable of use of high voltage DC current for example, 110-220 V DC. As a result of the capabilities of the power supply module, the inventive device is capable of operating on battery alone, or when, for example, in an emergency vehicle, on appropriate direct current supplied by the vehicle, for example, 12 to 24 Volts DC. Upon reaching a triage, emergency room, operating room in a hospital, etc., the device may be connected to the standard AC or DC current available in the particular locale.

The inventive device contains a control module, connected to a visual display. The visual display may be a standard LED display or its equivalent, and may also be a touch screen display to accept user input. The control module preferably accepts temperature readings from the exit heat transfer fluid, measured prior to exit of the heat transfer fluid from the exit port, from the inlet port, after the heat transfer fluid enters the device from the inlet port, and the temperature of the Peltier module. Based on these inputs, the control module adjusts the Peltier module current, the circulating pump speed, and the fan speed. In autothermal mode, these adjustments are made with respect to a body temperature measurement. The control module and power supply module are not necessarily separate components, and their respective functions may be combined, for example, on a single circuit board.

The inventive device preferably contains on and off switches, which may be configured, for example, as a single toggling switch, preferably a pressure (touch) sensitive switch. The device further contains a visual indicator to signify the status of the device as on or off. The visual indicator may be in the form of a backlit touch sensitive switch, may be indicated by one or more LEDs, for example a single LED which lights when the device is in the "on" state, or may be incorporated into the LED display, for example by the use of the words "on" or "off" or other designation.

The device preferably contains "cool" and "heat" switches, also preferably configured as pressure switches. The "cool" or "heat" status is reflected in the display. For full power use in either the cooling or heating mode, the display may simply indicate the status as "cool" or "heat." However, in many instances, a desired heating or cooling temperature may be designated. In this case, the controller may be configured to display a given temperature, for example, but not by limitation, 37° C., and repeated toggling of the heat or cool switches (or "down" and "up" switches or their equivalent), may be used to decrease or increase the set temperature, for example, but not by limitation, in 0.5° C. intervals. Alternatively, the display screen may be a touch screen with numeric keyboard to select a desired temperature.

The inventive device contains an inlet port and an outlet port for receiving and discharging heat transfer fluid. The ports are preferably configured to receive standard, liquid tight press in or turn-to-lock fittings. Preferably, the inlet and outlet ports remain open only so long as a fitting is in place in the respective port. This allows use without electrically operated valves, and also provides for filling the device with liquid by aid of the circulation pump, with the outlet port free of a fitting and therefore closed, and also prevents spilling heat transfer fluid from the ports when a cooling cuff is disconnected, even though the device is still in the "on" state.

The device preferably has associated therewith a heat transfer fluid line containing one individual tube for fluid discharged from the device and one individual tube for return fluid. While having separate flow passages, the tubes may be adjacent to each other in a single, integrated bitubular structure. These tubes are connected, at the proximal ends, to the respective inlet and outlet ports during use, and at the other end, to a thermal cuff/pad. The individual tubes are flexible, preferably, for example, of transparent polymer such as Tygon® tubing, and are preferably enclosed within an insulating sheath. The insulating sheath may be a simple fabric cover, or, for example, a fabric cover having an insulating foam layer within it, preferably also between the two fluid tubes. The heat transfer supply line is thus configured to assure that optimal use of the cooling and heating capabilities is achieved, with as little loss or gain of thermal energy from the environment as possible.

At the distal ends of the fluid supply line, the fluid supply and return lines are connected to a thermal cuff/pad containing fluid passages and connections for receiving supply fluid and discharge fluid. The thermal cuff/pads are preferably constructed of flexible material, for example, flexible polymer, to be able to conform to the body, and may include suitable closure means, including but not limited to hook and loop fasteners or straps, belts, snap fittings, etc. Examples of suitable thermal cuff/pads for use with the inventive device are disclosed, for example, in U.S. Pat. Nos. 5,507,792; 5,072,875; and 7,914,563, each of which is incorporated by reference herein.

One or more thermal cuff/pads may also be used with the inventive device. The device may be configured with multiple fluid inlet and exit ports, for example, but this is not preferred, as portability may suffer, and additional open/close valves will be required, increasing device complexity. Rather, it is preferred to simply divide the supply fluid by means of a simple "T" or "Y" connector, and recombine the return fluids by use of similar devices. More thermal cuff/pads can be connected for example by connection in series, T, Y . . . .

In use, the thermal cuff/pad is preferably installed on a patient at an arterial site, since such sites offer high blood flow and thus heating/cooling of the body is more efficient. Useful arterial sites include the neck region, the groin, etc.

In a preferred embodiment, a specially configured neck cuff is used, as shown in FIG. 3. This neck cuff is shaped to surround the neck region, and includes a hole in the front side thereof so that a tracheotomy tube can be inserted.

Preferred portable devices have a volume of <20,000 cm$^3$, more preferably <10,000 cm$^3$ (0.01 m$^3$), yet more preferably <8,000 cm$^3$ (0.008 m$^3$), and a weight of less than 7 Kg, more preferably less than 6 Kg, yet more preferably less than 4 Kg, and most preferably less than 3 Kg, without batteries installed. Preferred devices are capable of cooling 1 liter of water from 37° C. to 22° C. in less than one hour, are resistant to intrusion of water, and are capable of operating in high temperature, high humidity conditions.

To achieve light weight and protection from the environment, the device preferably has a cover of metal, polymer, or combination thereof, and most preferably includes internal or external walls of water resistant and heat insulating foam, such as a medium pore polystyrene or polyolefin foam. Preferably, all external connections are hermetically sealed within the foam. Foam with a density of 35 Kg/m$^3$ is suitable, for example. Most preferably, the foam forms a predominant portion of the cover of device, the top panel being separate. The foam container is preferably enclosed within a preferably close fitting fabric cover, equipped with suitable flaps to expose the battery compartment, and holes to allow for exit of air driven by the fan. The device preferably is able to meet FDA 510(k) requirements.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for increasing or decreasing the body temperature of a patient, comprising clothing a portion of the body with a thermal cuff/pad having passages therein to receive a heat transfer fluid, the heat transfer fluid having been heated or cooled by a portable, self-contained hypo/hyperthermy device, the device comprising:
   a) a power supply module comprising a battery charger and an inverter for converting alternating current to direct current;
   b) a heating/cooling module comprising one or more Peltier modules having a radiative heat sink on one side of the modules and a heating/cooling heat sink containing passages for the flow of a liquid heat transfer fluid on another side of the modules;
   c) a fluid reservoir in fluid communication with passages in the heating/cooling heat sink;
   d) an inlet port for receiving return fluid circulated external to the device, said inlet port in fluid communication with the fluid reservoir or with passages in the heating/cooling heat sink;
   e) an outlet port for discharging fluid which has been heated or cooled by the heating/cooling heat sink;
   f) a circulating pump which circulates fluid through the fluid reservoir, the passages in the heating/cooling heat sink, and inlet and outlet ports,
   g) a fan positioned to flow air past the radiative heat sink;
   h) a control module which receives one or more inputs of Peltier device temperature, temperature of fluid entering the inlet port, temperature of fluid exiting the outlet port, and/or a body temperature of a patient being heated or cooled using said device, and which varies one or more of circulation pump speed, fan speed, Peltier module current, and/or Peltier module polarity in response to said input(s);
   i) a first battery and a second battery; and
   j) a display device displaying one or more of on/off status, heating/cooling mode, set temperature, temperature of fluid discharged from the outlet port, temperature of fluid entering the inlet port, temperature of an external cuff through which fluid heated or cooled by the device flows, and/or a body temperature of a patient;

the method comprising:
   transferring fluid from the device to the thermal cuff/pad;
   while transferring the fluid, automatically switching a power source from the first battery to the second battery when the first battery is nearing a discharged state; and
   while transferring the fluid, replacing the first battery with a third battery.

2. The method of claim 1, wherein the portable hypo/hyperthermia device is proximate to the body of the patient, and is not connected to an external power source.

3. The method of claim 1, wherein said portion of the body includes an arterial site.

4. The method of claim 1, wherein said thermal cuff/pad is a cuff which surrounds a neck region of the body including at least a portion of the carotid artery.

5. The method of claim 4, wherein the cuff contains a hole for admitting a tracheotomy tube on a front side of the cuff.

6. The method of claim 1, wherein the body portion includes the groin.

* * * * *